United States Patent
Barnes et al.

(10) Patent No.: US 7,207,943 B2
(45) Date of Patent: Apr. 24, 2007

(54) SYNTHETIC ELEVATION APERTURE FOR ULTRASOUND SYSTEMS AND METHODS

(75) Inventors: Stephen R. Barnes, Bellevue, WA (US); Mirsaid Bolorforosh, Portola Valley, CA (US); D-L Donald Liu, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/807,681

(22) Filed: Mar. 24, 2004

(65) Prior Publication Data

US 2005/0215893 A1    Sep. 29, 2005

(51) Int. Cl.
*A61B 8/00* (2006.01)
(52) U.S. Cl. .................................... 600/447
(58) Field of Classification Search ............. 600/437, 600/441, 443, 447, 453–6, 458; 128/916; 73/625–626
See application file for complete search history.

(56) References Cited

U.S. PATENT DOCUMENTS

| | | | |
|---|---|---|---|
| 5,617,862 A * | 4/1997 | Cole et al. ................. | 600/459 |
| 6,132,375 A * | 10/2000 | Napolitano ................. | 600/443 |
| 6,464,638 B1 * | 10/2002 | Adams et al. ............... | 600/443 |
| 6,511,426 B1 * | 1/2003 | Hossack et al. ............. | 600/437 |
| 6,676,602 B1 | 1/2004 | Barnes et al. | |
| 6,733,453 B2 * | 5/2004 | Freiburger et al. .......... | 600/447 |
| 6,821,251 B2 * | 11/2004 | Alexandru .................. | 600/447 |

* cited by examiner

Primary Examiner—Francis J. Jaworski

(57) ABSTRACT

Using configurable arrays, synthetic aperture processes may be used along an elevation dimension for increasing resolution. The increased resolution is used for two-dimensional or three-dimensional imaging. Alternatively or additionally, wide band synthetic elevation aperture focusing processes, such as beamformation, are provided along the elevation dimension to increase resolution. In yet another alternative or additional embodiment, a transducer is rotated about a center of the transducer within the elevation and azimuth plane. An aperture associated with the transducer is mechanically or electronically rotated, and ultrasound data acquired associated with a plurality of different positions. The ultrasound data is then used for synthetic elevation aperture processing. In yet another alternative or additional embodiment, multiple scanning modes are provided. In a survey mode, imaging is provided without synthetic elevation aperture processing. For greater detailed imaging, imaging is responsive to synthetic elevation aperture processes with different elevation focusing and scanning.

12 Claims, 1 Drawing Sheet

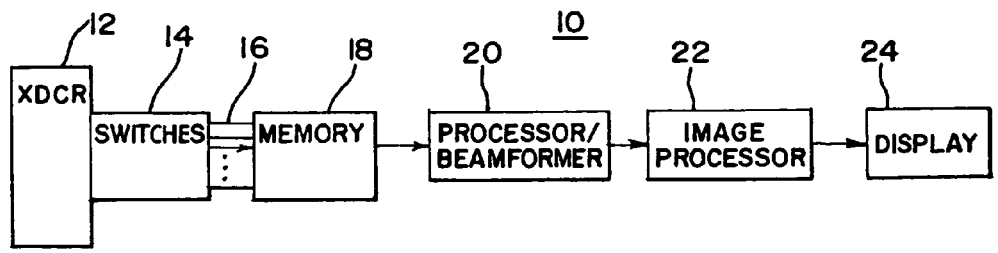
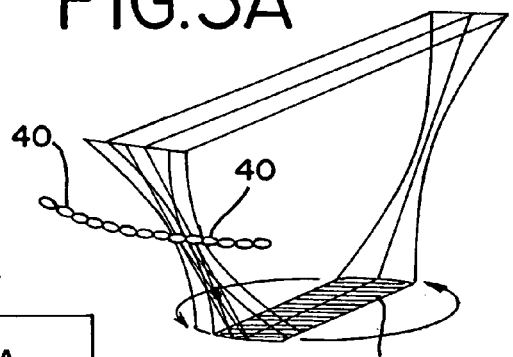
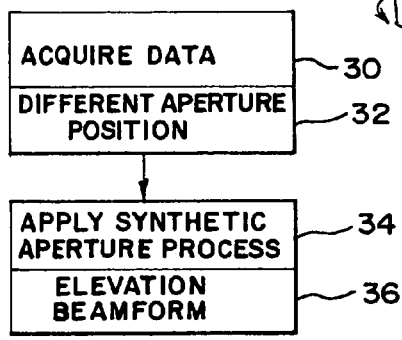
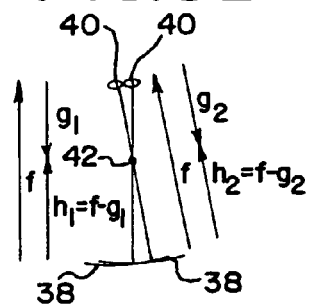
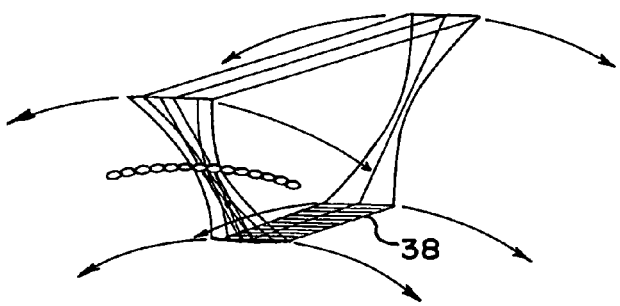
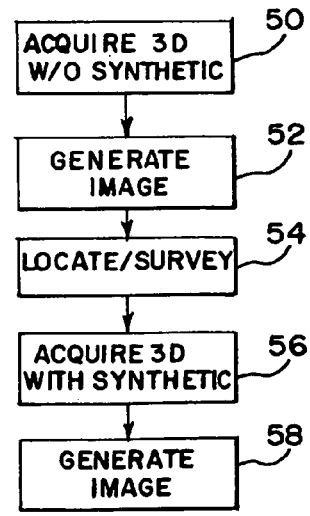

SYNTHETIC ELEVATION APERTURE FOR ULTRASOUND SYSTEMS AND METHODS

BACKGROUND

The present invention relates to synthetic elevation aperture processing. In particular, synthetic elevation aperture processes may provide increased resolution.

A volume is scanned acoustically for three-dimensional representations. The scan is performed with any of various arrays, such as one-dimensional, multi-row, or two-dimensional arrays. High resolution beamforming is typically provided in azimuth dimension. The linear one-dimensional array allows beamforming in a plane orthogonal to the array surface and passing through the center of every element. In the elevation dimension or orthogonal to the imaging plane, the resolution is affected by the amount of elevation focusing. One-dimensional arrays use a fixed mechanical focus in the elevation dimension. Curved elements along an elevation dimension may increase the elevation focus. A lens or other structure may also be used to provide a fixed focal length in the elevational dimension. A different elevation beamwidth is provided for different depths, such as a narrowest beamwidth at a focal point, a widest beamwidth at the deepest depth for imaging or scanning, and an elevation beamwidth equal to the elevation aperture width at the surface of the array.

For scanning a volume, the one-dimensional array is translated or rotated to sequentially scan different planes within the volume. For example, the array is rotated about a normal vector at the center of the array aperture. In the direction of rotation or a generally elevation direction, poor resolution may be provided due to the wide point spread function or elevation beamwidth close to the array and at the deeper depths for imaging. Since beamformation is provided within the imaging plane or along a radius of the scanned conical volume, high resolution is provided in the radial direction parallel to the array surface. Similarly for other rotations, such as associated with a wobbler transducer, or translations, the resolution along an elevation dimension may be poor relative to the resolution provided by beamforming within the imaging planes.

BRIEF SUMMARY

By way of introduction, the preferred embodiments described below include methods and systems for forming a synthetic elevation aperture. Using configurable arrays, synthetic aperture processes may be used along an elevation dimension for increasing resolution. The increased resolution is used for two-dimensional or three-dimensional imaging. Alternatively or additionally, wide band synthetic elevation aperture processes, such as beamformation, are provided along the elevation dimension to increase resolution. In yet another alternative or additional embodiment, a transducer is rotated in the plane of the transducer aperture about a center of the transducer. An aperture associated with the transducer is mechanically or electronically rotated, and ultrasound data acquired associated with a plurality of different angular orientations. The ultrasound data is then used for synthetic elevation aperture processing. In yet another alternative or additional embodiment, multiple scanning modes are provided. In a survey mode, imaging is provided without synthetic elevation aperture processing. For greater detailed imaging once a region of interest has been identified, imaging is responsive to synthetic elevation aperture processes.

In a first aspect, a method is provided for forming a synthetic elevation aperture. At least first and second sets of ultrasound data are acquired. The first set of ultrasound data is associated with a different elevation position than the second set of ultrasound data. A beam is formed across the synthetic elevation aperture as a function of the first and second sets of ultrasound data. The beamformation is a broadband process.

In a second aspect, a system is provided for forming a synthetic elevation aperture. A memory is operable to store at least first and second sets of ultrasound data associated with different elevation positions. A beamformer is operable to form a beam across a synthetic elevation aperture as a function of the ultrasound data. The beamformation is a broadband process.

In a third aspect, a method is provided for forming a synthetic elevation aperture. A multi-dimensional transducer array is configured with a first interconnection of elements. A first set of ultrasound data is acquired as a function of the first interconnection. The multi-dimensional transducer array is configured with a second interconnection of elements. The second interconnection of elements corresponds to a different elevation aperture than the first interconnection. A second set of ultrasound data is acquired as a function of the second interconnection. A synthetic elevation aperture process is applied to the first and second sets of ultrasound data.

In a fourth aspect, a system is provided for forming a synthetic elevation aperture. A plurality of switches is operable to interconnect elements of a multi-dimensional transducer array into a plurality of macro elements. A plurality of system channels are operable to be connected with respective macro elements. A processor is operable to apply a synthetic elevation aperture process to the ultrasound data associated with different interconnections of the elements.

In a fifth aspect, a method is provided for forming a synthetic elevation aperture. An aperture is rotated substantially within an elevation-azimuth plane. Sets of ultrasound data are acquired. One set is associated with one position of the aperture and another set is associated with a different position of the aperture. A synthetic elevation aperture focusing process is applied to the sets of ultrasound data.

In a sixth aspect, a method is provided for imaging with synthetic elevation aperture processing. Data is acquired representing a volume in a mode free of synthetic elevation aperture processing. An image is generated as a function of the data. A second set of data is acquired representing a volume in a second mode, in which the elevation aperture is focused differently than in the first mode in order to achieve a transmit focus with a wider angular spectrum. The second set of data is processed by synthetic elevation aperture focus processing, and another image is generated as a function of the data. The two acquisitions are performed within the same imaging session.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for forming a synthetic elevation aperture;

FIG. 2 is a flow chart diagram of one embodiment of a method for forming a synthetic elevation aperture;

FIG. 3A is a graphical representation of an aperture rotated in an elevation-azimuth plane in one embodiment;

FIG. 3B is a graphical representation of the relationships of the focal region to an array and the desired synthetic delays as a function of spatial location;

FIG. 4 is a graphical representation of one embodiment showing translation and rotation of a transducer array, such as associated with a wobbler transducer; and FIG. 5 is a flow chart showing one embodiment of a method for imaging with synthetic elevation aperture processing.

DETAILED DESCRIPTION OF THE DRAWINGS AND PRESENTLY PREFERRED EMBODIMENTS

FIG. 1 shows a system 10 for forming a synthetic elevation aperture. The system 10 includes a transducer 12, a plurality of switches 14, a plurality of system channels 16, a memory 18, a processor or beamformer 20, an image processor 22 and a display 24. Additional, different or fewer components may be provided, such as providing the system 10 without the switches 14. In one embodiment, the entire system 10 is provided within an imaging device, such as a medical diagnostic ultrasound system. In other embodiments, part of the system 10 is a separate component, such as a work station.

The transducer 12 is an array of piezoelectric or capacitive membrane transducers. The transducer 12 includes elements distributed on any of various now known or latter developed grid patterns. For example, a one-dimensional curvilinear, linear, phased-linear or other transducer is provided. For a 1D transducer, only one channel is used in the elevation direction and is connected to a constant elevation length element. In another embodiment, the transducer elements are distributed in a multi-dimensional array, such as a two-dimensional array of N×M elements where N and M are equal or non-equal.

In other embodiments, the transducer 12 is a 1.25D, 1.5D or 1.75D array. 1.25D, 1.5D, 1.75D, and 2D arrays are configurable. For example, the switches 14 are used to select between connecting a center row of elements with outer elements to increase or decrease the elevation aperture in a 1.25D array (e.g., configuration elevation length for a given channel). As another example, the switches 14 are operable to connect system channels 16 to any one or more of multiple rows of elements to effect an elevation translation of the active aperture in use across the face of the transducer. In this latter example, the transducer may be a 1D, 1.25D, 1.5D, 1.75D, or 2D. For a 1.5D transducer, more than one system channel 16 is used in the elevation direction connected to more than one element in the elevation direction where each system channel connects to a section of the elevation length of sub-element and to a mirror image sub-element on the alternate side of the aperture elevation center, implementing mirror symmetric delays about the elevation centerline. This configuration allows elevation beamforming to only one single plane through the aperture elevation centerline. For a 1.75D transducer, more than one system channel 16 is used in the elevation direction connected to more than one element in the elevation direction where each system channel connects to only one contiguous section of the elevation element, allowing independent delays for each section of aperture. This configuration allows elevation beamforming and limited steering to multiple planes in elevation where the degree of steering is limited by the elevation length of the independent elements. For 2D transducers, the same configuration as 1.75D may be used except that the elevation length is smaller and/or the number of elements in elevation is much greater, allowing many more independent image planes in elevation covering a much larger volume.

In yet another embodiment, the transducer 12 is a multi-dimensional or two-dimensional array with configurable connections. Using the switches 14, any of various apertures may be formed on the face of the array, such as a one-dimensional aperture, 1.75 dimensional or other distributions of elements. For example, the configurable multi-dimensional array disclosed in U.S. Pat. No. 6,676,602, the disclosure of which is incorporated herein by reference, is provided. By providing a selectable one-dimensional array on the multi-dimensional transducer, a configurable one-dimensional array is provided. Non-configurable arrays may also be used in alternative embodiments.

For one-dimensional arrays or multiple-dimensional arrays with limited elevation steering, structure for measuring a position of the transducer 12 is provided. For example, the transducer 12 may be placed in various elevation positions in a frame, the transducer 12 may be motorized to provide evenly spaced shift or rotation in elevation position (e.g. a wobbler transducer array), or guides or other sources of information are provided for indicating a proper elevation position in a hand-held transducer 12. Other elevation positioning or measuring devices may be used, such as magnetic position sensors or by using ultrasound data to determine translation and/or rotation. For using ultrasound data, speckle tracking, or correlation or decorrelation (i.e., amount of correlation) may be used for elevation positioning. For two-dimensional arrays steerable in both azimuth and elevation directions, the beamformer parameters or other steering information is used to identify data associated with different positions.

The switches 14 are operable to interconnect the elements of the transducer 12 into a plurality of macro elements for a configurable transducer 12. The switches 14 are microelectromechanical devices, relays, transistors or other now known or latter developed switches. For example, any switches disclosed in U.S. Pat. No. 6,676,602 for selectively configuring macro elements in a multi-dimensional array are used. In one embodiment, the switches 14 are positioned on a face of the transducer array, but may be positioned within a transducer assembly, within a transducer probe, within a transducer substrate, or within an imaging system spaced from the transducer 12. The switches 14 are operable to connect different system channels 16 to different elements or macro elements of the transducer array 12 in one embodiment, but separate switches may be used for channel connection in other embodiments. The switches 14 are circuits for interconnection. Other circuits may be used, such as time division multiplexing, sub-array mixing, partial beamforming or other circuits connecting a plurality of elements over a single channel for one or more sub apertures.

The plurality of system channels 16 are operable to be connected with respective macro elements or other elements of the transducer array 12 in one embodiment. The system channels 16 are transmit beamformer, receive beamformer, or both transmit and receive beamformer channels. System channels provide separate electrical connection to the imaging system 10 for different elements of the transducer 12.

Separate electrical connection may be provided by multiplexing on a same conductor or by having separate conductors.

The memory 18 is a buffer, first-in first-out memory, RAM, hard drive, removable media, or other now known or latter developed memory. In one embodiment, the memory 18 is a CINE memory, but memories using other formats may be used. The memory 18 is positioned prior to the beamformer 20 or after the beamformer 20 as a function of the type of data operated on by the processor or beamformer 20. For beamforming simultaneously along multiple dimensions, the memory 18 is positioned as shown prior to the processor 20. For beamforming along an elevation dimension as a synthetic elevation aperture focusing process, the memory 18 is positioned within the beamformer 20, prior to the beamformer 20 or after the beamformer 20 with a feedback loop. Data is then beamformed along two different dimensions sequentially.

The memory 18 is operable to store different sets of ultrasound data. As used herein, a set of ultrasound data includes one or more samples or analog signals. For example, one set of ultrasound data corresponds to a line or a plurality of scan lines beamformed within an azimuth and range plane. In another example, a set of ultrasound data corresponds to data from elements of the transducer 12 prior to any beamforming. The sets of data may include a portion of a frame of data, a portion of a line of data, an entire line of data, an entire frame of data, multiple frames of data or other grouping of ultrasound data. The sets are associated with different elevation positions. For example, one set of data is acquired with an aperture at one position at a given time. The aperture is then repositioned to a different elevation position and another set of ultrasound data is acquired at a different time. A different elevation aperture position is provided by having one or more elements of an array offset an elevation partially or entirely. For example, some overlap of elevation aperture may be provided where a rotation or translation of the transducer is less than an elevation width of the transducer 12.

The processor or beamformer 20 is operable to apply a synthetic elevation aperture focusing process to the sets of ultrasound data. In one embodiment, the processor 20 is a filter, such as disclosed in U.S. Pat. No. 6,132,375, the disclosure of which is incorporated herein by reference, with or without beamformer capability. An application specific integrated circuit, general processor, control processor, digital signal processor, or analog processor may be used. In another embodiment, the processor 20 is a beamformer, such as a transmit, receive or both transmit and receive beamformer. As a transmit beamformer, the processor 20 connects with the transducer without passing through the memory 18. The transmit beamformer includes amplifiers for applying apodization profiles, delays for applying a relative delay profiles and waveform generators, such as transistors, memories, digital-to-analog converters or other know known or later developed devices for generating a transmit waveform. As a receive beamformer, the processor 20 includes amplifiers for applying apodization, delays or phase rotators for applying delay profiles and a summer for combining information from different channels. The processor 20 is operable to form a beam across a synthetic elevation aperture as a function of different sets of ultrasound data. For example, data is acquired sequentially at different elevation positions. The data is then beamformed across the elevation dimension to provide a synthetic aperture. Beamformation is a broadband process. In one embodiment, the processor 20 is operable to perform a delay and sum beamformation. In another embodiment, the processor 20 performs frequency-domain beamformation along the elevation aperture.

For use with a configurable transducer 12, the processor 20 is operable to apply a synthetic elevation aperture process to sets of ultrasound data associated with different interconnections of elements. The different interconnections provide different elevation aperture positions, such as positions associated with translation or rotation of the aperture or positions associated with increased or decreased elevation width. The processor 20 is operable to apply delay and sum or frequency-domain beamformation to sets of the data associated with different interconnections of elements. Alternatively, the processor 20 applies filtering as a function of beam width using data from different elevationally positioned apertures as a synthetic elevation aperture process.

In yet another embodiment, the processor 20 is operable to perform a multi-dimensional beamformation. Beams are formed using data along the azimuth and elevation dimensions. Using interpolation in the frequency domain or a time domain process, three-dimensional filtering of broadband data is provided.

The image processor 22 is a B-mode detector, Doppler detector, flow detector, scan converter, temporal filter, spatial filter, three-dimensional render processor or other now known or latter developed imaging device. The image processor 22 generates signals for display. The signals are generated from ultrasound data subject to synthetic elevation aperture processing. In an alternative embodiment, the image processor 22 is operable with data free of or without synthetic elevation aperture processing.

The display 24 is a CRT, LCD, monitor, projector or other or other now known or latter developed display device. The display 22 displays three-dimensional representations or two-dimensional images responsive to ultrasound data. In one embodiment, the three-dimensional representation is responsive to synthetic elevation aperture processing. As a result, greater detail or spatial resolution along an elevation dimension is provided than without synthetic elevation aperture processing. Where beamformation is used along the elevation aperture, broadband data with greater content than narrow band synthetic elevation aperture filtering, may be used. In an alternative embodiment, an image is generated free of synthetic elevation aperture processing.

FIG. 2 shows one embodiment of a method for forming a synthetic elevation aperture. Different, additional, or fewer acts may be provided in the same or different order. In acts 30 and 32, ultrasound data is acquired associated with different elevation aperture positions. In acts 34 and 36, a synthetic aperture process is applied along the elevation dimension to the acquired data. In the embodiment shown in FIG. 2, elevation beamforming 36 is the synthetic aperture process applied, but other processes such as filtering may be provided.

In act 30, different sets of ultrasound data are acquired. In one embodiment, the acquired ultrasound data is digital or analog signals representing information received at each element of the transducer 12. For example, ultrasound data for each of the elements of an array spaced along an azimuth dimension is received and stored. In another embodiment, the acquired ultrasound data is beamformed data. For example, ultrasound data acquired with different elevation positions as beamformed along the azimuth and range dimensions. In one embodiment, the beamformed data is in-phase and quadrature data or radiofrequency data maintaining relative phase information.

Each set of ultrasound data is associated with a different elevation position. Any of rotation, translation or both rotation and translation of an aperture may be used in act 32 to provide a different elevation position. Increasing or decreasing an elevation width may also provide a different elevation position. In one embodiment, the aperture is positioned into different positions without movement of a transducer, such as by electronic positioning. In other embodiments, the transducer 12 is moved to provide a different elevation position, such as using a wobbler transducer, other mechanical movement or through free hand scanning.

A different set of ultrasound data is received and stored by positioning the elements in a different elevation position. Each data acquisition associated with a different elevation position provides data to be treated as a different element in a synthetic array. Along an azimuth dimension of a one-dimensional aperture, an actual azimuth aperture is provided. Where the one-dimensional array is then sequentially positioned to different elevation positions, the sequentially acquired data is used to form a synthetic elevation array. The elevation aperture geometry used to take each data set is considered to be a synthetic array element. The magnitude of movement of the aperture along the elevation dimension between sequential scans provides an element pitch where a point source is used. For a finite aperture focused source, the delays are calculated as discussed herein.

In another example embodiment of positioning the aperture to different elevation positions in act 32, FIG. 3A shows spinning a transducer about its center, such as rotating a one-dimensional phased array 38 in an elevation-azimuth plane. A multi-dimensional array may alternatively be used. At one position of the array 38, ultrasound data is acquired. Since the aperture is a one-dimensional phased array, the aperture is focused in two dimensions, in the azimuth direction by electronic beamforming and in the elevation direction by curvature of the aperture or a lens. The point spread function of the beam at the focal region 40 is at a minimum dimension in elevation. The data is beamformed along the azimuth and range plane associated with each particular position within the image plane or may be provided as element data. Data from any point along the beam is associated with a beamwidth due to elevation aperture characteristics. The array 38 is then rotated clockwise or counterclockwise with an elevation, i.e. angular, step. In one embodiment, the largest extent of the elevation step is greater than the wavelength of the acoustic waveforms divided by four and less than the elevation dimension of the point spread function of the beam at the focal region 40. Greater or lesser steps may be used. The rotation within the elevation-azimuth plane allows acquisition of ultrasound data associated with a different elevation positions for synthetic elevation aperture. The rotation is performed electronically or mechanically. For example, electronic rotation is provided by using selected elements in a multi-dimensional array as the aperture, such as with a configurable array. Mechanical rotation is provided by physically moving the array.

By rotating the array, the point spread function such as represented by the focal region 40 translates along a circular path to a new location. Data from any point along the beam at the new rotated elevation position is used to represent data taken from an aperture in elevation having characteristics defined by the new point spread function at the new focus location. The data sets represent data taken from elements of a synthetic array located along the circular path at the focal distance.

In another embodiment of acquiring data in act 30 associated with different elevation aperture positions of act 32, a configurable multi-dimensional transducer array is configured to provide translation or rotation of the aperture. Electronics are used to move the aperture to a different position. For example, a two-dimensional array is used to generate a one-dimensional, 1.25D, 1.5D or 1.75D array using interconnection of elements to form macro elements as disclosed in U.S. Pat. No. 6,676,602. Elements are switchably interconnected on the multi-dimensional array to form a macro element. The macro elements formed are a function of the desired aperture position. For example, two or more elements are connected together that have similar delays based on a position of a plane or the steering direction within a plane. The macro elements are then maintained for steering along any of various scan lines within the same plane, but may be selected as a function of a steering line or steering angle. Ultrasound data is then acquired associated with one interconnection of elements. The multi-dimensional transducer array is then reconfigured with a different interconnection of elements to provide a different elevation aperture. Elements are switched to form different macro elements as a function of the position of a plane in azimuth and range. The plane is associated with a different elevation position. The aperture is electronically rotated about the face of a two-dimensional array. Alternatively, a 1.25D, 1.5D or 1.75D is used to reconfigure elements or switchably interconnect elements for providing a different elevation aperture width, in addition to, or free of any rotation or translation. Ultrasound data is then acquired as a function of the different interconnections of elements.

FIG. 4 shows translation and rotation of the array 38, such as associated with a wobbler transducer array. The synthetic elevation aperture process described herein may be applied to translation and rotation as shown in FIG. 4 as an alternative to the rotation shown in FIG. 3A. Additionally, free hand movement of the transducer array may be provided in any of the rotation or translations shown in FIGS. 3A, 4 or others. The position of the array 38 is measured, such as within accuracy within one-tenth of a wavelength, but greater or lesser accuracies may be provided. For example, at 2.5 MHz, a tenth of a wavelength in tissue is approximately 600 microns, giving a tenth wavelength accuracy of 60 microns.

In act 34, a synthetic aperture process is applied to the sets of ultrasound data. Each set represents a different element along the elevation dimension for forming the synthetic elevation aperture. In one embodiment, the process applied is the filtering disclosed in U.S. Pat. No. 6,132,375, the disclosure of which is incorporated herein by reference. The filtering includes axial position dependent filtering applied along the elevation direction in the temporal domain or by means of a Fourier transform matched filtering. Other temporal or frequency domain synthetic aperture filtering processes may be used.

In another embodiment, the synthetic elevation aperture process is a wideband process, such as forming a beam along an elevation dimension or beamforming with one of delay and sum beamformation or frequency-domain beamformation in act 36 (e.g., synthetic elevation aperture focusing process). Other time domain or frequency domain synthetic aperture processing methods now known or later developed may be used. Time domain synthetic elevation aperture focusing processing is provided by delay and summing of waveforms with a dynamic delay and weighting. Synthetic beamforming using beam data from overlapping elevation beamwidths may improve resolution. By overlapping of the focal point for each elevation position, the beamwidths overlap in the near field and far field so that resolution along all depths may be improved.

FIG. 3B graphically represents one embodiment for determining delays as a function of elevation position for delay-and-sum beamforming. The ultrasound data is beamformed along the azimuth and range dimensions. Each set of azimuth-beamformed ultrasound data is associated with a different elevation aperture position. For beamforming across the synthetic elevation aperture, relative delays are calculated. By considering the synthetic aperture to be located at the focus 40 of the beam, the delay may be calculated without determining a location on the transducer array 38 or aperture closest to the synthetic aperture point 42 to be beamformed. For each point 42 of interest, a relative delay is calculated relative to the elevation location of the array. The delay is calculated as a function of the distance F from the array to the corresponding focal point 40. The distance may be the same or different for different elevation positions of the array 38. The distance from the focal point 40 to the point 42 of interest for synthetic elevation aperture beamforming is determined, such as based on the known spatial relationship of the desired point 42 and the focal regions 40. The delay calculated from propagation back from the focus to the sample volume 42 is used to determine the delay associated with the array 38 to the point of interest 42. The delay h provides the synthetic aperture delay for forward propagation from the aperture 38. The synthetic aperture beamforming delay h is the propagation time from the point on the array 38 which is collinear with the point of interest 42 and the focal region 40. This location on the array 38 is associated with the desired stationary phase or relative delay of echoes from the sample volume or point of interest 42. FIG. 3B shows the delay calculations to sample volume 42 for two different positions of aperture 38. The calculation may be performed for more than two positions. For each sample volume 42, the process is repeated for each set of data of each different elevation aperture position for the synthetic beamformation.

The delays may alternatively be calculated through iteration or algorithms used for aberration correction. Correlation or other processes are used to determine a shift resulting in a brightest speckle or highest data values upon summation. The delays are shifted to find the highest contrast. The shifted delay estimates are then used for registration of the data samples from the sets of ultrasound data for summation or to complete beamformation.

The relative delays are then applied to each set of ultrasound data. The relative delay identifies a data sample of the set associated with or closest to the point 42 of interest. Due to sampling differences, the selected data sample corresponding to the desired delay may be spatially offset short of or past the point 42 of interest. A phase shift may be applied to shift the selected data sample to correspond to the desired spatial location or point 42. The selected and/or phase shifted data from each set of data is then summed to provide beamforming along the elevation dimension.

In another embodiment, complex addition of coherent data is performed as a function of the desired spatial location or point 42. Two, three, four or more data samples from a single set or from multiple sets of ultrasound data associated with a single elevation position or multiple elevation positions are identified as a function of the above described delays. The data closest to the desired spatial location 42 within the one or multiple sets are then interpolated in magnitude after application of relative phase shifts. This complex addition weights the data through interpolation in phase and magnitude to provide a data sample to represent the elevation beamformed information at the desired point 42.

The process is repeated to provide synthetic elevation aperture beamforming for a plurality of points 42. For example, transmit and receive processes for a scan line along an azimuth and range plane are obtained. The data is beamformed and saved as complex or coherent data. The process is repeated for each depth along a scan line. The scan line process is then repeated for each scan line within the plane. Once a scan at one elevation position is complete, the aperture is positioned to a different elevation position. The process is then repeated for beamforming along a plurality of scan lines. Once all of the sets of data are acquired, the sets of data are used to form a synthetic elevation aperture from the complex beamformed data. The elevation data is synthesized to increase resolution, such as synthesizing for points 42 in between spatial locations associated with acquired data. Although one specific example has been given here, the data acquisition and computational processes may be done in any order. For example, in an alternate embodiment where there is sufficient elevation agility associated with the aperture, the scanning may proceed intermingling data acquisition in various elevation positions and various azimuth scan lines to reduce blurring of fast moving targets.

For delay-and-sum beamforming, dynamic delays, aperture size and weighting or apodization may be used to achieve optimal focusing. Delay-and-sum beamforming may use broadband signals as opposed to being a narrow band approximation of filtering. Since both the transmit and receive apertures are synthesized, dynamic transmit and receive focusing may be achieved in the synthetic process. In alternative embodiments, the dynamic focusing is provided for receive only or transmit only operation. In alternative embodiments, apodization is not applied along the synthetic elevation aperture.

Similarly, synthetic elevation aperture may be used for annular arrays to improve transmit focusing without multiple transmits. The annular array is moved in two dimensions, and the synthetic aperture focusing may be two-dimensional. If the annular array is moved in one dimension, then the synthetic aperture focusing is one-dimensional.

In another example of elevation beamforming in act 36 to form a synthetic elevation aperture, a beam is formed with a frequency-domain beamformation. Any conventional radar synthetic aperture processing in the frequency domain may be used. In one embodiment, a spatial-temporal Fourier transform is applied to received data. Spatial-temporal Fourier transform is applied to the data within a two-dimensional or planar acquisition. The transform is applied to each of the different sets of data. The data is then interpolated within the frequency domain from being evenly sampled in the temporal frequency domain to being evenly sampled in the frequency domain or the spatial frequency along the Z or axial direction. The interpolation is applied without phase rotation in one embodiment. In other embodiments, the interpolation also includes phase rotation, such as associated with filtering. The interpolated data is then inversed transformed with an inverse spatial-temporal Fourier transform. The resulting data provides the desired image or information beamformed along the elevation dimension. Various filtering and apodization schemes may be applied in the space-time or spatial-temporal frequency domains to reduce side lobe and truncation errors.

In another embodiment of beamforming in the elevation dimension to provide wideband synthetic aperture processing in act 36, a two-dimensional beamformation along both the elevation and azimuth dimensions is provided. The beamformation is performed for each range sample, resulting in three-dimensional filtering of broadband data. Suppose the rf point spread function in the vicinity of point (x0, y0, z0) is denoted as g(x,y,z; x0,y0,z0), where x is along the azimuth direction, y is along elevation direction, and z is along depth direction. The imaging process is represented as:

$$o(x,y,z)=g(x,y,z; x0, y0, z0)***i(x,y,z)$$

where i is input, o is output, and *** denotes 3-dimensional convolution in x, y, and z. In the frequency domain, this is expressed as:

$$O(fx, fy, fz)=G9fx, fy, fz; x0, y0, z0)\ I(fx, fy, fz)$$

Given a known point spread function, g(x, y, z), which can be obtained by simulation or experimental measurement, a 3-dimensional deconvolution or matched filtering can be used to reduce the image smearing effect of g(x, y, z). For example, with 3-D Wiener filtering, the output p(x,y,z) would be computed as the inverse Fourier transform of P(fx,fy,fz) given by $$P(fx,fy,fz)=O(fx,fy,fz)\ G^*(fx,fy,fz)/(|G(fx,fy,fz)|^2+N(fx,fy,fz))$$

where G* is the complex conjugate of G, and N(fx,fy,fz) is estimated noise power contained in O(fx,fy,fz). If the noise power is high (N is large), Wiener filtering reduces to matched filtering, while if noise power is low (N is negligible), Wiener filtering reduces to inverse filtering. Additional filtering may be performed to further enhance image contrast resolution and to reduce noise.

Ultrasound data from each element is acquired and saved for a given elevation position. Data associated with different scan lines for the elevation aperture position is acquired. The array is moved to a different elevation position and data from each of the elements for a plurality of scan lines is acquired. Multi-dimensional beamformation is then used to form data samples in both elevation and azimuth as a function of depth.

FIG. 5 shows one embodiment of a method for imaging with synthetic elevation aperture processing. Additional, different or fewer acts may be provided in the same or different order. For example, imaging with synthetic elevation aperture processing is provided without other modes of operation, such as acts 50 and 52.

The acts shown in FIG. 5 are performed in a same imaging session, such as being interleaved on a frame-by-frame basis or being performed sequentially. The user configures the ultrasound imaging system for three-dimensional or two-dimensional imaging. Two different modes are provided, a survey mode and a high resolution mode. The survey mode is used for identifying a region of interest. Upon locating the region of interest, the user activates the high resolution mode, such as by depressing a button. Within the same imaging session, the user locates a region of interest and then generates high resolution images associated with the region of interest.

In act 50, ultrasound data associated with a three-dimensional volume or two-dimensional plane is acquired without synthetic elevation aperture processing. For example, ultrasound data is acquired for imaging a volume in a survey mode free of synthetic elevation processing. During the survey mode, the elevation apertures are focused as much as possible without synthetic processing. For example, a 1.25, 1.5 or 1.75D array uses some electronic control to focus along the elevation dimension. Alternatively, the mechanical or one dimensional focus is used. As yet another alternative, a two-dimensional array is used to focus in the elevation dimension. Less elevation focusing may be provided. A larger elevation aperture size may be provided for providing a more narrow focus in elevation. For acquiring data of a three-dimensional volume for rendering three-dimensional images, the elevation step size associated with moving or repositioning the aperture along the elevation dimension is about one-half of the two-way response associated the –6 dB beamwidth in the elevation direction. Fifty percent or greater overlap of elevationally spaced beams is provided to satisfy the Nyquist sampling criteria.

In act 52, an image is generated in response to the acquired data. For example, a three-dimensional representation is rendered from data acquired over a volume. In alternative embodiments, the data is rendered from a planar scan.

In act 54, the user surveys a region of interest or patient to identify a desired organ or other location for high resolution imaging. The acts of 50 and 52 are repeated in real time, but may be repeated at a slower rate for locating a region of interest in the survey.

In act 56, additional ultrasound data representing the same or different volume or plane is acquired in another mode of operation, such as a high resolution mode of operation. The ultrasound data is associated with synthetic elevation aperture processing. Using one or more of the processes discussed above, the high resolution mode includes synthetic elevation aperture processing. For acquiring the data, a wider focus, i.e. with a larger angular spatial spectrum, is used for act 56 than for act 50. Defocusing in elevation may be performed electronically or mechanically with an aperture having a narrower elevation dimension. For example, only a center row of a 1.25, 1.5 or 1.75 dimensional array is used. A wider focus may be provided by using more focusing or defocusing delays with a multi-dimensional array as an alternative to limiting the use to a single row. For a one-dimensional array, a mechanical shutter may be used to reduce the elevation extent of the elements for a wider focus. In yet other alternative embodiments, the focus for act 56 is similar to the focus used for act 50. The elevation aperture step size or difference between each elevation aperture position is less for acquiring data in the high resolution mode. The minimal useful elevation step size is the wavelength divided by 4. Alternatively, larger step sizes may be used. Alternatively, the step size in elevation is greater for act 56 than for act 50.

In act 58, an image is generated from the data acquired in act 56. Since the data acquired in act 56 has a synthetic elevation aperture process applied, a greater elevation resolution may be provided than for the image generated in act 52. The synthetic elevation aperture process can create an elevation aperture size effectively larger than the physical extent in elevation of the elements used to acquire the data. The synthetic focusing elevation resolution is limited by the angular spatial spectrum of the element beam pattern. By using defocused elements or smaller elements in the elevation direction, a larger angular spatial spectrum may be provided, achieving a higher resolution, one that may be similar to or comparable to resolution in the azimuth direction. Alternatively, a wider angular spatial spectrum may be provided by using electronic focusing of multi-row array with a larger delay curvature in the elevation direction.

For any of the three-dimensional imaging discussed above, any now known or later developed rendering may be used. Data representing a volume is acquired after reconstruction through beamformation, interpolation or both beamformation and interpolation to a three-dimensional grid. Alpha blending, maximum intensity projection, minimum intensity projection, surface rendering or other rendering techniques are performed on the reconstructed data. A three-dimensional representation is generated as a function of the rendering.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for forming a synthetic elevation aperture, the method comprising:
   (a) acquiring at least first and second sets of ultrasound data, the first set of ultrasound data associated with a different elevation position than the second set of ultrasound data;
   (b) forming a beam across a synthetic elevation aperture as a function of the first and second sets of ultrasound data, the forming being a broadband process; and
   (c) generating a three-dimensional representation as a function of the beam.

2. The method of claim 1 wherein (b) comprises forming with delay-and-sum beamformation.

3. The method of claim 2 wherein (b) comprises:
   (b1) determining a first delay for a particular spatial location as a function of a first distance from an array to a first data set focal point and a second distance from the first data set focal point to the particular spatial location; and
   (b2) applying the first delay to a first data sample from the first set of ultrasound data;
   (b3) determining a second delay for the particular spatial location as a function of a third distance from the array to a second data set focal point and a fourth distance from the second data set focal point to the particular spatial location; and
   (b4) applying the second delay to a second data sample from the second set of ultrasound data; and
   (b5) summing the first and second data samples.

4. The method of claim 2 wherein (b) comprises performing complex addition of coherent data as a function of data samples spatial location relative to a desired spatial location.

5. The method of claim 1 wherein (b) comprises forming with frequency-domain beamformation.

6. The method of claim 5 wherein (b) comprises:
   (b1) applying a spatial-temporal Fourier transform;
   (b2) interpolating in the frequency domain; and
   (b3) applying an inverse spatial-temporal Fourier transform.

7. The method of claim 1 wherein (a) comprises acquiring the first and second sets of ultrasound data, the first and second sets of ultrasound data being for elements of an array spaced along an azimuth dimension, and wherein (b) comprises performing two-dimensional beamfomation along the elevation and azimuth dimensions.

8. A method for forming a synthetic elevation aperture, the method comprising:
   (a) acquiring at least first and second sets of ultrasound data, the first set of ultrasound data associated with a different elevation position than the second set of ultrasound data; and
   (b) forming a beam across a synthetic elevation aperture as a function of the first and second sets of ultrasound data, the forming being a broadband process;
   wherein (a) comprises acquiring beamfornied data as the first and second sets of ultrasound data, and wherein (b) comprises forming the beam from the beamformed data and
   (c) generating an image as a function of the beam.

9. The method of claim 1 wherein (a) comprises:
   (a1) acquiring the first set of ultrasound data with a first aperture;
   (a2) acquiring the second set of ultrasound data wit a second aperture, the second aperture rotated within an elevation-azimuth plane relative to the first aperture, the rotation such that foci of the first and second apertures overlap.

10. A system for forming a synthetic elevation aperture, the system comprising:
    a memory operable to store at least first and second sets of ultrasound data the first set of ultrasound data associated with a different elevation position than the second set of ultrasound data;
    a beamformer operable to form a beam across a synthetic elevation aperture as a function of the first and second sets of ultrasound data, the forming being a broadband process; and
    an image processor operable to generate a three-dimensional image as a fraction of the beam.

11. The system of claim 10 wherein the first and second sets of data correspond to receiving at different times, and wherein the beamformer is operable to perform delay-and-sum beamformation along an elevation aperture.

12. A method for forming a synthetic elevation aperture, the method comprising:
    (a) acquiring at least first and second sets of ultrasound data the first set of ultrasound data associated with a different elevation position than the second set of ultrasound data;
    (b) forming a plurality of different elevationally spaced beams across a synthetic elevation aperture as a function of the first and second sets of ultrasound data, the forming being a broadband process; and
    (c) generating an image as a function of the beam.

* * * * *